United States Patent
Höfle et al.

(10) Patent No.: US 6,359,140 B1
(45) Date of Patent: Mar. 19, 2002

(54) EPOTHILONES WITH MODIFIED SIDE CHAIN

(75) Inventors: Gerhard Höfle, Braunschweig; Michael Sefkow, Potsdam, both of (DE)

(73) Assignee: Gesellschaft fuer Biotechnologische Forschung mbH (GBF), Braunschweig (DE)

( * ) Notice: Subject to any disclaimer, the term of this patent is extended or adjusted under 35 U.S.C. 154(b) by 0 days.

(21) Appl. No.: 09/376,754

(22) Filed: Aug. 17, 1999

Related U.S. Application Data

(63) Continuation of application No. PCT/EP98/01060, filed on Feb. 25, 1998.

(30) Foreign Application Priority Data

Feb. 25, 1997 (DE) .......................... 197 07 505

(51) Int. Cl.$^7$ ............................ C07D 493/04
(52) U.S. Cl. ........................................ 548/204
(58) Field of Search .......................... 548/204

(56) References Cited

FOREIGN PATENT DOCUMENTS

| WO | WO 93/10121 | 5/1993 | |
|----|-------------|--------|---|
| WO | 98/25929 | * 6/1998 | .................. 548/204 |

OTHER PUBLICATIONS

"Designed Epothilones: Combinatorial Synthesis, Tubulin Assembly Properties, and Cytotoxic Action Against Taxol–Resistant Tumor Cells", XP–002070869, Nicolaou et al., Angew Chem. Int. Ed. Engl. 36, No. 19, pp. 2097–2103, 1997.

International Search Report for PCT/EP98/01060 dated Jul. 29, 1998.

* cited by examiner

*Primary Examiner*—Robert Gerstl
(74) *Attorney, Agent, or Firm*—Marshall, Gerstein & Borun

(57) ABSTRACT

Epothilones with a modified side chain and process for the preparation thereof are disclosed.

4 Claims, No Drawings ns with modified side chain

This is a continuation of International Application No. PCT/EP98/01060 filed Feb. 25, 1998, the entire disclosure of which is incorporated herein by reference.

Epothilones A and B have been disclosed; cf. for example, DE 4 138 042, WO 93 10 121 and WO 97 19 086.

The mentioned art suggests said epothilones as therapeutic agents. In PNAS USA, 95 (1998) 1369–1374 epothilones are described as useful therapeutic agents. According to Angew. Chem., Int. Ed., 36 (1997) 2097–2103 an extensive library of such compounds is provided based on their therapeutic effects.

The invention now relates to a process for the preparation of epothilones which are modified in the 16,17-position, in which process the starting materials are 3,7-protected or unprotected epothilones A or B and a) these are hydrogenated on the 16,17-double bond or b) subjected to an addition reaction with halogen on the 16,17-double bond or c) epoxidized on the 16,17-double bond and, if appropriate, the resulting epoxide is reduced to give the 16-alcohol.

The process according to the invention may be characterized in that, in method (a), hydrogenation is affected with diimine or hydrogen and a heterogeneous or homogenous metal catalyst or in method (c), epoxidation is affected with a peracid or a dioxirane.

Furthermore, the invention concerns a process for the preparation of 2,3-unsaturated epothilbne N-oxides in which either (i) 3,7-protected epothilones A or B are converted into an N-oxide in a manner known per se and, the 3-substituent is eliminated by a base to give the 2,3-double bond, or (ii) 7-protected or 7-unprotected epothilones A or B which have a double bond in the 2,3-position are converted into an N-oxide in a manner known per se and, if appropriate, the resulting N-oxide is subjected to O-alkylation and an O-alkylation product is obtained.

Furthermore, the invention relates to a process for the preparation of epothilone N-oxides in which 3,7-protected or unprotected epothilones A or B are converted into an N-oxide in a manner known per se and, if appropriate, the resulting N-oxide is subjected to O-alkylation and an O-alkylation product is obtained.

This process according to the invention may be characterized in that N-oxidation is performed with peracid or a dioxirane and electrophilic alkyl, aryl or heteroaryl reagents, in particular methyl iodide or trimethyloxonium tetrafluoroborate, are used for the optional O-alkylation.

Furthermore, this process according to the invention may be characterized in that a resulting N-oxide is subjected to a Katada reaction, in particular as described in Houben-Weyl, Volume E7b, page 646.

Furthermore, this process according to the invention may be characterized in that the Katada reaction is performed with an activated carboxylic acid derivative, in particular carboxylic anhydride or carboxylic acid chloride.

Furthermore, this process according to the invention may be characterized in that the Katada reaction is carried out with acetic anhydride and, if appropriate, the 21-acetoxyepothilones obtained are cleaved in a manner known per se to give 21-hydroxyepothilones A or B (epothilones E and F, respectively).

Furthermore, this process according to the invention may be characterized in that the optional cleavage process is performed hydrolytically or enzymatically.

Furthermore, the invention relates to a process for the preparation of epothilones which are modified in the C19-position, in which process 3,7-protected or unprotected epothilones A or B are metalated in the C19-position and captured with electrophilic reagents in a manner known per se as alkyl-, aryl-, heteroaryl-, halogen-, oxygen- or sulphur-substituted epothilones which are modified in the C19-position.

This process according to the invention may be characterized in that metalation is performed using butyllithium.

Furthermore, the invention relates to a process for the preparation of epothilones which are modified in the C27-position, in which process the allyl group (C17, C16 and C27) is substituted in a manner known per se on the C27-methyl group by a hetero atom.

This process according to the invention may be characterized in that the C27-methyl group is substituted by a bromine atom, in particular with the aid of N-bromo-succinimide, and, if appropriate, the resulting bromide is converted into a C27-hydroxy compound.

Finally, the invention relates to compounds prepared by the process according to the invention.

Experiment 1

Diepoxyepothilone A. 1a)

A solution of epothilone A (5 mg, 10 $\mu$mol) in acetone (1 ml) was treated at 0° C. with dimethyldioxirane (0.4 ml, 28 $\mu$mol, 0.07 M in acetone). The solution was brought to room temperature in the course of a few hours and was stirred for 20 hours at this temperature. Since TLC confirmed that starting material was still present, more dimethyldioxirane (0.25 ml, 17 $\mu$mol) was added, and the reaction mixture was again stirred for 20 hours at room temperature. The solvent was removed and the residue was purified by means of PLC (0.25×200×200 mm, 10% MeOH:CH$_2$Cl$_2$). The following were isolated:

1. 1.4 mg (27%) of diepoxyepothilone A (3:2 epimer mixture on C16–C17). $R_f$ 0.63 (10% MeOH:CH$_2$Cl$_2$); $R_t$: 6.79 (isomer 1) and 7.39 (isomer 2) min (RP 18, 250×4 mm, MeOH:H$_2$O 65:35, 1 ml/min) ; MS: (m/z)=510 (M$^+$); $^1$H NMR (400 MHz, CDCl$_3$, selected signals, isomer 1): $\delta$=6.96 (s, 1H, H-19), 5.48 (dd, J=12.2 and 2.5 Hz, 1H, H-15), 4.37 (dbr, J=10.7 Hz, 1H, H-3), 4.10 (s, 1H, H-17), 3.67 (dd, J=5.6 and 2.5 Hz, 1H, H-7), 3.14 (qd, J=6.6 and 2.5 Hz, 1H, H-6), 3.00 (ddd, J=9.7, 3.6 and 2.5 Hz, 1H, H-13), 2.88 (dt, J=8.6 and 3.6 Hz, 1H, H-12), 2.71 (s, 3H, H-21), 2.53 (dd, J=13.7 and 11.7 Hz, 1H, H-2a), 1.41 (s, 3H, H-22), 1.27 (s, 3H, H-26), 1.17 (d, J=6.6 Hz, 3H, H-24), 1.08 (s, 3H, H-23), 0.97 (d, J=7.1 Hz, 3H, H-25); (isomer 2) $\delta$=6.98 (s, 1H, H-19), 5.11 (dd, J=11.7 and 2.5 Hz, 1H, H-15), 4.27 (dbr, J=10.7 Hz, 1H, H-3), 4.14 (s, 1H, H-17), 3.06 (qd, J=6.6 and 2.9 Hz, 1H, H-6), 2.96 (ddd, J=9.7, 3.6 and 2.5 Hz, 1H, H-13), 2.31 (dt, J=14.7 and 2.0 Hz, 1H, H-14a), 1.36 (s, 3H, H-22), 1.15 (d, J=6.6 Hz, 3H, H-24), 1.14 (s, 3H, H-26), 1.07 (s, 3H, H-23).

2. 0.8 mg (16%) of epothilone A N-oxide. $R_f$ 0.44 (10% MeOH:CH$_2$Cl$_2$); $R_t$: 4.25 min (RP 18, 250×4 mm, MeOH:H$_2$O 65:35, 1 ml/min); MS: (m/z)=510 (M$^+$); $^1$H NMR: see method 1

Experiment 2

Dihydroepothilone A. (1c)

Palladium on charcoal (5 mg, 10%) was added to a solution of epothilone A (11 mg, 22 $\mu$mol) in ethanol (2 ml) and the black suspension was exposed to an H$_2$ atmosphere for 24 hours at room temperature. Since TLC indicated that the reaction was not yet complete, a further portion of Pd/C was added and the reaction mixture was stirred for a further 20 hours under an $H_2$ atmosphere. The products were separated by means of PLC (1×200×200 mm, 10% MeOH:$CH_2Cl_2$). The following were isolated:

1. 0.5 mg (5%) of dihydroepothilone A. $R_f$ 0.60 (10% MeOH:$CH_2Cl_2$); $R_{t:}$ 10.80 min (RP 18, 250×4 mm, MeOH:$H_2O$ 65:35, 1 ml/min); MS: (m/z)=496 ($M^+$), 478, 407, 308; $^1$H NMR (400 MHz, $CDCl_3$, selected signals): δ=7.05 (d, J=6.6 Hz, 1H, OH), 6.77 (s, 1H, H-19), 5.23 (dd, J=12.4 and 2.3 Hz, 1H, H-15), 4.42 (ddd, J=11.7, 6.6 and 3.0 Hz, 1H, H-3), 3.70 (ddd, J=5, 3 and 2 Hz, 1H, H-7), 3.12 (qd, J=6.6 and 3.0 Hz, 1H, H-6), 3.07 (d, J=12.7 Hz, 1H, H-17a), 2.96 (ddd, J=9.7, 3.6 and 2.0 Hz, 1H, H-13), 2.91 (ddd, J=9.7, 3.6 and 2.6 Hz, 1H, H-12), 2.68 (s, 3H, H-21), 2.51 (dd, J=13.7 and 11.7 Hz, 1H, H-2a), 2.24 (d, J=12.7 Hz, 1H, H-17b), 2.19 (m, 1H, H-16), 2.13 (dd, J=13.7 and 3.0 Hz, 1H, H-2b); 1.35 (s, 3H, H-22), 1.15 (d, J=6.6 Hz, 3H, H-24), 1.09 (s, 3H, H-23), 0.99 (d, J=7.1 Hz, 3H, H-25), 0.93 (d, J=6.6 Hz, 3H, H-26).

2. 8 mg (72%) of 15-deoxydihydroepothilonic acid. $R_f$ 0.10 (10% MeOH:$CH_2Cl_2$).

Experiment 3
16-Hydroxyepothilone A. (1b)

Palladium on charcoal (10 mg, 10%) was added to a solution of diepoxyepothilone A (7 mg, 14 μmol), 1:1 epimer mixture on C-16 in ethanol (2 ml) and the black suspension was exposed to an $H_2$ atmosphere for 24 hours at room temperature. Since TLC indicated that the reaction was not yet complete, a further portion of Pd/C was added and the reaction mixture was stirred for a further 80 hours under an $H_2$ atmosphere. The products were separated by means of PLC (1×200×200 mm, 10% MeOH:$CH_2Cl_2$). The following were isolated:

1. 3 mg (43%) of 16-hydroxyepothilone A (isomer 1). $R_f$ 0.38 (10% MeOH:$CH_2Cl_2$); $R_{t:}$ 6.65 min (RP 18, 250×4 mm, MeOH:$H_2O$ 65:35, 1 ml/min); $^1$H NMR (400 MHz, $CDCl_3$, selected signals): δ=6.85 (s, 1H, H-19), 5.02 (dd, J=11.7 and 2.0 Hz, 1H, H-15), 4.38 (dbr, J=11.2 Hz, 1H, H-3), 3.67 (dd, J=4 and 3 Hz, 1H, H-7), 3.14 (qd, J=6.8 and 3.0 Hz, 1H, H-6), 2.95 (d, J=15.3 Hz, 1H, H-17a), 2.89 (d, J=15.3 Hz, 1H, H-17b), 2.89 (ddd, J=10.2, 3.6 and 2.0 Hz, 1H, H-13), 2.81 (ddd, J=9.7, 3.6 and 2.5 Hz, 1H, H-12), 2.70 (s, 3H, H-21), 2.53 (dd, J=15.8 and 11.7 Hz, 1H, H-2a), 2.14 (dd, J=15.8 and 2.0 Hz, 1H, H-2b), 2.08 (dt, J=14.3 and 2.0 Hz, 1H, H-14a), 1.39 (s, 3H, H-22), 1.25 (s, 3H, H-26), 1.19 (d, J=6.6 Hz, 3H, H-24), 1.05 (s, 3H, H-23), 0.99 (d, J=7.1 Hz, 3H, H-25).

2. 3 mg (43%) of 16-hydroxyepothilone A (isomer 2). $R_f$ 0.31 (10% MeOH:$CH_2Cl_2$); $R_{t:}$ 6.10 min (RP 18, 250×4 mm, MeOH:$H_2O$ 65:35, 1 ml/min); $^1$H NMR (300 MHz, $CDCl_3$, selected signals): δ=6.85 (s, 1H, H-19), 5.21 (dd, J=11.3 and 1.9 Hz, 1H, H-15), 4.42 (dbr, J=10.5 Hz, 1H, H-3), 3.71 (sbr, 1H, H-7), 3.21 (d, J=14.3 Hz, 1H, H-17a), 3.13 (qd, J=6.8 and 3.0 Hz, 1H, H-6), 3.09 (dt, J=9.8 and 3.4 Hz, 1H, H-13), 2.87 (dt, J=9.4 and 3.0 Hz, 1H, H-12), 2.73 (d, J=14.3 Hz, 1H, H-17b), 2.68 (s, 3H, H-21), 2.63 (dd, J=16.6 and 11.7 Hz, 1H, H-2a), 2.27 (dt, J=14.7 and 2.3 Hz, 1H, H-14a), 2.24 (dd, J=16.6 and 2.6 Hz, 1H, H-2b), 1.39 (s, 3H, H-22), 1.22 (s, 3H, H-26), 1.19 (d, J=6.8 Hz, 3H, H-24), 1.05 (s, 3H, H-23), 0.99 (d, J=7.2 Hz, 3H, H-25).

Epothilone A N-oxide (2a): 100 mg of 70% m-chloroperbenzoic acid in 0.5 ml of dichloromethane were added to 100 mg of epothilone A in 1 ml of dichloromethane. After the mixture has been stirred for 6 hours at room temperature, it is diluted with dichloromethane and extracted by shaking in succession with sodium sulphite solution to destroy excess peracid and with sodium bicarbonate solution. The solvent is evaporated in vacuo, and the residue is separated by preparative HPLC on a Nucleosil RP-18 column (250×20 mm, eluent methanol/water 60:40). Yield 60 mg of colourless oil.

$R_f$=0.60 (silica gel TLC aluminium foil, eluent dichloromethane/methanol 9:1);

ESI-MS (neg. ions) m/z 510;

UV (methanol): lamda max. 240 nm;

$^{13}$C NMR ($CDCl_3$): C-1 170.5, C-2 39.9, C-3 70.8, C-4 55.1, C-5 221.4, C-6 40.9, C-7 72.9, C-8 37.6, C-9 31.8, C-10 22.8, C-11 28.0, C-12 58.0, C-13 55.8, C-14 32.2, C-15 75.5, C-16 144.5, C-17 111.4, C-18 143.4, C-19 110.3, C-20 145.6, C-21 13.5, C-22 15.4, C-23 23.3, C-24 12.0, C-25 16.5, C-27 18.2 ppm;

$^1$H NMR ($CDCl_3$): 2a-H 2.12 dd, 2b-H 2.47 dd, 3-H 4.55 dd, 3-OH 6.48 broad, 6-H 3.25 dq, 7-H 3.72 dd, 8-H 1.81 m, 9a-H 1.34 m, 9b-H 1.56 m, 10-$H_2$ 1.48 m, 11a-H 1.27 m, 11b-H 1.87 m, 12-H 2.92 ddd, 13-H 2.98 m, 14a-H 1.67 ddd, 14b-H 2.23 d, 15-H 5.33 d, 17-H 6.82 s, 19-H 7.09 s, 21-$H_3$ 2.61 s, 22-$H_3$ 1.02 s, 23-$H_3$ 1.42 s, 24-$H_3$ 1.18 d, 25-$H_3$ 0.99 d, 27-$H_3$ 2.04 s ppm.

21-Acetoxyepothilone A (=21-acetylepothilone E) (3a): 0.05 ml of 2,6-di-tert-butylpyridine and 0.1 ml of acetic anhydride are added to 50 mg of epothilone A N-oxide (2a) in 0.5 ml of dichloromethane. After the mixture has been heated at 75° C. for 15 minutes, solvent and reagents are evaporated in vacuo and the residue is separated by preparative HPLC on Nucleosil RP-18 (250×20 mm, eluent methanol/water 60:40). Yield 30 mg of colourless oil.

$R_f$ 0.50 (silica gel TLC aluminium foil, eluent dichloromethane/methanol 95:5);

ESI-MS (neg. ions) m/z 552;

UV (methanol): lamda max. 210, 250 nm;

$^1$H NMR ($CDCl_3$, signals different with respect to 2a): 15-H 5.45 dd, 17-H 6.60 s, 19-H 7.15 s, 21-$H_2$ 5.35 s, $CH_3CO$ 2.15 s ppm.

Epothilone E (3b): 1 drop of concentrated ammonia solution is added to 10 mg of 21-acetoxyepothilone A (3a) in 0.5 ml of methanol, and the mixture is heated for 1 hour at 40° C. and is evaporated to dryness in vacuo. The residue is separated by preparative TLC. Yield 6 mg, identical with an authentic sample of epothilone E.

Experiment 4
19-Methylepothilone A. (4b)

A solution of epothilone A (15 mg, 30 μmol) in THF (1 ml) was treated at −90° C. with n-butyllithium (100 μl, 160 μmol, 1.6 M in hexane). The solution immediately turned golden orange. After the reaction solution had been stirred for 15 minutes at −90° C., it was treated with methyl iodide (100 μl, 1.6 mmol). The resulting pale greenish-yellow solution was warmed to −30° C. and quenched with buffer pH=7.0 (2 ml). The emulsion was brought to pH 6 with 0.1 N hydrochloric acid. After the mixture had been saturated with solid NaCl, the aqueous phase was extracted with $CH_2Cl_2$ (2×5 ml) and ethyl acetate (5 ml), the combined organic phases were dried over $MgSO_4$ and filtered, and the solvent was removed on a Rotavap. Purification was done by PLC (1×200×200 mm, 10% MeOH;$CH_2Cl_2$) and HPLC (RP 18, 250×16 mm, MeOH:$H_2O$ 65:35). The following were isolated:

1. 2.5 mg (17%) of 19-methylepothilone A. $R_f$ 0.50 (10% MeOH:$CH_2Cl_2$); $R_{t:}$ 11.70 min (RP 18, 250×4 mm, MeOH:$H_2O$ 65:35, 1 ml/min); MS: (m/z)=508 ($M^+$), 420, 320; $^1$H NMR (300 MHz, $CDCl_3$, selected signals): δ=6.41 (s, 1H, H-17), 5.46 (dd, J=9.0 and 2.3 Hz, 1H, H-15), 4.15 (dd, J=10.5 and 3.0 Hz, 1H, H-3), 3.77 (dd, J=8 and 4 Hz, 1H, H-7), 3.20 (qd, J=6.8 and 4.5 Hz, 1H, H-6), 3.04 (dt, J=7.5 and 3.8 Hz, 1H, H-13), 2.91 (dt, J=7.5 and 3.8 Hz, 1H, H-12), 2.61 (s, 3H, H-21), 2.51 (dd, J=14.4 and 10.5 Hz, 1H, H-2a), 2.38 (dd, J=14.4 and 3.0 Hz, 1H, H-2b), 2.32 (s, 3H, H-27), 2.15 (ddd, J=15.1, 3.8 and 3.0 Hz, 1H, H-14a), 2.01

(d, J=1.5 Hz, 3H, H-26), 1.91 (dt, J=15.1 and 8.8 Hz, 1H, H-14b); 1.34 (s, 3H, H-22), 1.16 (d, J=6.8 Hz, 3H, H-24), 1.10 (s, 3H, H-23), 1.00 (d, J=6.8 Hz, 3H, H-25).

2. approx. 50% of epothilone A

Experiment 5

19-Bromoepothilone A. (4a)

A solution of epothilone A (25 mg, 50 μmol) in THF (2.5 ml) was treated at −90° C. with n-butyllithium (160 μl, 225 μmol, 1.6 M in hexane). The solution immediately turned golden orange. After the mixture had been stirred for 15 minutes at −90° C., N-bromosuccinimide (27 mg, 150 μmol), dissolved in THF (0.5 ml), was added. The solution discoloured slowly. The reaction mixture, now a pale brownish colour, was warmed to −30 ° C. and brought to pH 6.5 with 0.1 N hydrochloric acid (1 ml). After the mixture had been saturated with solid NaCl, the aqueous phase was extracted with $CH_2Cl_2$ (2×5 ml) and ethyl acetate (5 ml), the combined organic phases were dried over $MgSO_4$ and filtered, and the solvent was removed on a Rotavap. Purification was done by PLC (1×200×200 mm, 10% $MeOH:CH_2Cl_2$) and HPLC (RP 18, 250×16 mm, $MeOH:H_2O$ 65:35). The following were isolated:

1. 2.6 mg (9%) of 19-bromoepothilone A. $R_f$ 0.53 (10% $MeOH:CH_2Cl_2$); $R_t$: 20.78 min (RP 18, 250×4 mm, $MeOH:H_2O$ 65:35, 1 ml/min); MS: (m/z)=574 and 572 ($M^+$), 556, 554, 468, 466, 386, 384, 341; $^1H$ NMR (300 MHz, $CDCl_3$, selected signals): δ=6.43 (s, 1H, H-17), 5.46 (dd, J=8.7 and 2.3 Hz, 1H, H-15), 4.13 (ddd, J=9.4, 6.0 and 3.8 Hz, 1H, H-3), 3.80 (dd, J=8 and 4 Hz, 1H, H-7), 3.38 (d, J=6.0 Hz, 1H, OH), 3.22 (qd, J=6.8 and 5.3 Hz, 1H, H-6), 3.05 (dt, J=8.3 and 4.1 Hz, 1H, H-13), 2.91 (dt, J=7.5 and 3.7 Hz, 1H, H-12), 2.66 (s, 3H, H-21), 2.55 (dd, J=14.7 and 9.4 Hz, 1H, H-2a), 2.47 (dd, J=14.7 and 3.8 Hz, 1H, H-2b), 2.16 (d, J=1.1 Hz, 3H, H-26), 2.14 (dt, J=14.7 and 3.8 Hz, 1H, H-14a), 1.90 (dt, J=15 and 8.3 Hz, 1H, H-14b); 1.34 (s, 3H, H-22), 1.17 (d, J=6.8 Hz, 3H, H-24), 1.11 (s, 3H, H-23), 1.01 (d, J=6.8 Hz, 3H, H-25).

2. approx. 60% of epothilone A

SYNTHESIS EXAMPLES 1a to 5a

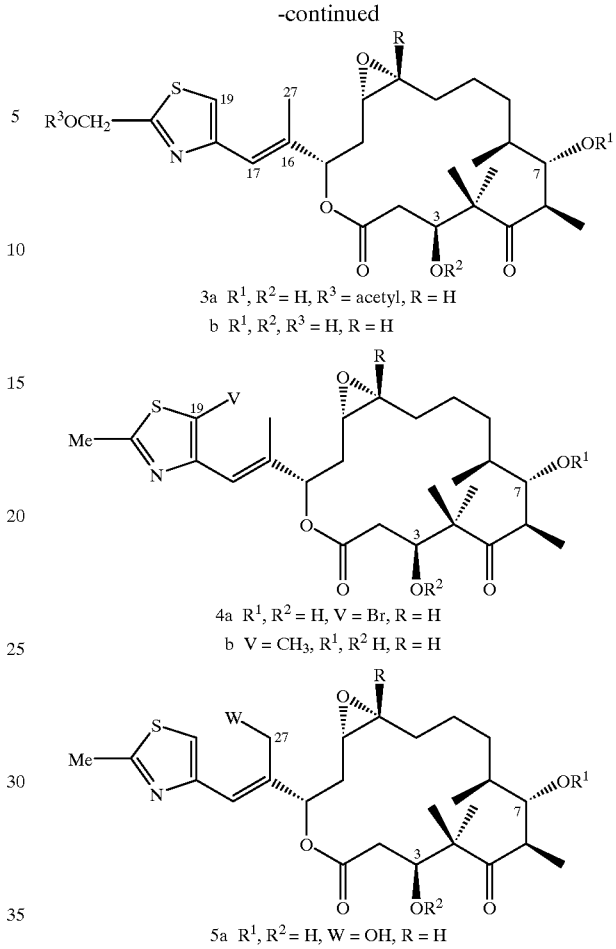

1a $R^1, R^2 = H, X, Y = —O—, R = H$
b $R^1, R^2 H, X = OH Y = H, R = H$
c $R^1, R^2 = H, X = H Y = H, R = H$

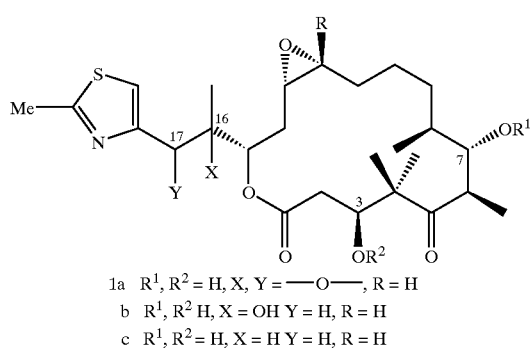

2a $R^1, R^2 = H, Z = O^-, R = H$
b $R^1, R^2 = H, Z = OCH_3 BF_4^-, R = H$

-continued

3a $R^1, R^2 = H, R^3 = acetyl, R = H$
b $R^1, R^2, R^3 = H, R = H$

4a $R^1, R^2 = H, V = Br, R = H$
b $V = CH_3, R^1, R^2 H, R = H$

5a $R^1, R^2 = H, W = OH, R = H$

What is claimed is:

1. Compounds obtained by a process for the preparation of epothilones which are modified in the 16,17-position, wherein the starting materials are 3,7-protected or unprotected epothilones A or B, said method comprising the steps of:

a) hydrogenating said epothilones on the 16,17-double bond or b) halogenating said epothilones on the 16,17-double bond or c) epoxidizing said epothilones on the 16,17-double bond and optionally reducing the resulting epoxide to give the 16-alcohol.

2. Epothilone-N-oxide (epothilone A-N-oxide), having the formula:

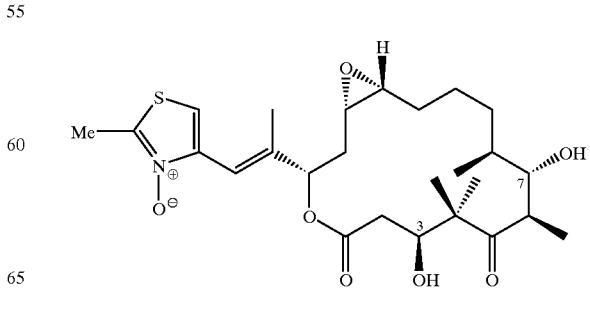

3. Compound of the following formula:
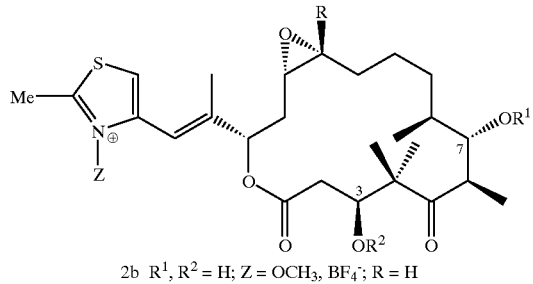
2b  R$^1$, R$^2$ = H; Z = OCH$_3$, BF$_4^-$; R = H
4. Epothilone-N-oxide (epothilone B-N-oxide), having the formula:
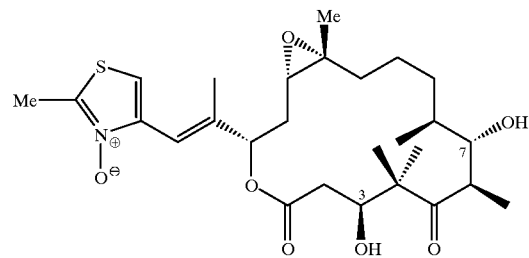
* * * * *